(12) United States Patent
Wu et al.

(10) Patent No.: US 6,420,703 B1
(45) Date of Patent: Jul. 16, 2002

(54) METHOD FOR FORMING A CRITICAL DIMENSION SEM CALIBRATION STANDARD OF IMPROVED DEFINITION AND STANDARD FORMED

(75) Inventors: Chia-Fang Wu, Taiwan (TW); Ming-Chun Chou, Vancouver, WA (US)

(73) Assignee: Taiwan Semiconductor Manufacturing Co., Ltd, Hsin Chu (TW)

( * ) Notice: Subject to any disclaimer, the term of this patent is extended or adjusted under 35 U.S.C. 154(b) by 0 days.

(21) Appl. No.: 09/585,190

(22) Filed: Jun. 1, 2000

(51) Int. Cl.⁷ .......................... G01N 23/00; G21K 7/00
(52) U.S. Cl. ................ 250/311; 250/252.1; 250/306; 250/492.1; 156/643
(58) Field of Search .......................... 250/306, 307, 250/492.2, 311, 252.1, 492.1; 280/306; 156/643

(56) References Cited

U.S. PATENT DOCUMENTS 5,126,574 A * 6/1992 Gallagher ............... 250/492.22
5,920,067 A * 7/1999 Cresswell et al. .......... 250/306

* cited by examiner

Primary Examiner—John R. Lee
Assistant Examiner—David Vanore
(74) Attorney, Agent, or Firm—Randy W. Tung

(57) ABSTRACT

A method for forming a critical dimension scanning electron microscope calibration standard and standard formed are disclosed. In the method, a plurality of metal lines, i.e. formed of a suitable metal such as W, Pt, Au, Ta or Ti, for use as critical dimension SEM calibration is formed by a focused ion beam technique to produce straight, narrow lines with an edge roughness of less than 30 nm in a 0.5 μm length. The plurality of metal lines has a line width uniformity of less than 20 nm in a length of 20 μm.

20 Claims, 2 Drawing Sheets

METHOD FOR FORMING A CRITICAL DIMENSION SEM CALIBRATION STANDARD OF IMPROVED DEFINITION AND STANDARD FORMED

FIELD OF THE INVENTION

The present invention generally relates to a method for forming a calibration standard and standard formed and more particularly, relate to a method for forming a critical dimension scanning electron microscope (SEM) calibration standard by a focused ion beam (FIB) technique and the standard formed.

BACKGROUND OF THE INVENTION

In the study of electronic materials and processes for fabricating such materials into an electronic structure, a specimen of the electronic structure is frequently used for microscopic examination for purposes of failure analysis and device validation. For instance, a specimen of an electronic structure such as a silicon wafer is frequently analyzed in scanning electron microscope (SEM) and transmission electron microscope (TEM) to study a specific characteristic feature in the wafer. Such characteristic feature may include the circuit fabricated and the defect formed during the fabrication process. An electron microscope is one of the most useful equipment for analyzing the microscopic structure of semiconductor devices.

In preparing specimens of an electronic structure for electron microscopic examination, various polishing and milling processes can be used to section the structure until a specific characteristic feature is exposed. As device dimensions are continuously reduced to the sub-half-micron level, the techniques for preparing specimens for study in an electron microscope have become more important. The conventional methods for studying structures by an optical microscope cannot be used to study features in a modern electronic structure due to its unacceptable resolution.

In a focused ion beam (FIB) technique, focused ion beams are used to either locally deposit or remove materials. When the cluster impacts the surface of an electronic structure, the cluster disintegrates into atoms which are then scattered over the surface to remove a surface layer of the material. Typical ion beams have ea focused spot size of smaller than 100 nm when produced by a high intensity source. Sources of such high intensity ions can be either liquid metal ion sources or gas field ion sources. Both of these sources have a needle type form that relies on field ionization or evaporation to produce the ion beam. After the ion beam is produced, it is deflected in a high vacuum and directed to a desired surface area. The focused ion beams can be suitably used in the semiconductor processing industry in a cutting or attaching method to perform a circuit repair, a mask repair or a micromachining process. A cutting process is normally performed by locally sputtering a surface with a forced ion beam.

In an ion beam milling process, when a material is selectively etched by a beam of ions such as Ga+ focused to a sub-micron diameter, the technique is often referred to as focused ion beam etching or milling. FIG milling ins a very useful technique for restructuring a pattern on a mask or an integrated circuit, anc for diagnostic cross-sectioning of microstructures. In a typical FIB etching process, a beam of ions such as Ga+ is incident onto a surface to be etched and the beam can be deflected to produce a desirable pattern. The focused ion beam can be used to bombard a specimen surface such that a cavity can be formed on the surface of an electronic surface to review a characteristic feature of the structure for electron microscopic examination.

The FIB technique utilizes a primary beam of ions for removing a layer of material at a high current, and for observing the surface that was newly formed at a low current. The observation of the surface is made by detecting the secondary electrons emitted from the sample surface when the surface is bombarded by the ions. A detector is used to receive the secondary electrons emitted from the surface to form an image. The FIB method, even though can not produce an image of a high resolution like that obtainable in a SEM/TEM, can be used to sufficiently identify a newly formed cross-sectional surface which may contain the characteristic feature to be examined. The capability of the FIB technique for making observations down to a resolution of 5~10 nm enables the cutting of a precise plane in an electronic structure such that it may later examined by a SEM or TEM technique at a higher resolution than that capable with FIB.

In modern ULSI semiconductor devices, particularly in sub-0.18 nm devices, metal lines used for connecting devices on a chip becomes extremely thin such that the use of SEM for analysis is frequently required. When a SEM is utilized for analyzing a high density IC device, it can be used for either measurement or for analysis. A SEM that is used for measurements of critical line width is frequently called CD-SEM wherein CD stands for critical dimension. The major functions for a CD-SEM is to perform a critical dimension measurement of important material layers such as SiN, polysilicon, contact window and metal connecting lines. This is because the line width of these layers has a great influence on the properties of the IC device. Frequently, In-line CD-SEM utilizes field emission electron gun and operates under low acceleration voltage, i.e. lower than 1 kV, such that the electrical properties of the IC device is not damaged. A CD-SEM apparatus is constructed in a complex manner to fulfill its high accuracy and measurement stability. As a result, the cost of a CD-SEM apparatus is significantly higher than a traditional SEM apparatus.

Before a critical dimension on a semiconductor device can be determined by the CD-SEM technique, the CD-SEM apparatus must first be calibrated by a calibration standard of known line width. Such calibration is frequently carried out by using polysilicon lines deposited of a known width and thickness on a semiconductor substrate. In a conventional calibration standard of polysilicon lines, the standard is produced by first sputter depositing a polysilicon layer on the substrate, then photo-masking in a photolithography process defining the lines. The polysilicon lines are then etched in a dry etching or a wet etching process and the photomask is then removed. A typical calibration standard using polysilicon lines is shown in FIG. 1.

The polysilicon lines 12 which are deposited on a substrate 10 have a width of approximately 0.3 nm and a thickness of approximately 0.5 nm. Since the etching process, regardless a dry etching or a wet etching process, never produces a vertical sidewall, the white lines 14 indicate a tapered sidewall. In the formation of the polysilicon lines 12, two major problems are observed. First, a poor line width uniformity is normally obtained. For instance, as shown in FIG. 1, a line width uniformity of about 14 nm is observed in a single line, and a line width uniformity of about 0.01 nm with a 3 sigma is observed in 20 measurements. It is therefore possible to obtain a line width that has better uniformity.

A second problem encountered in forming a CD-SEM calibration standard with polysilicon lines is the roughness of the line edge obtained. For instance, as shown in FIG. 1, the polysilicon line 12 has a typical line edge roughness of about 20 nm in a 0.5 μm length. The cause of the line edge roughness is the large grain size of the photomask utilized which limits the line edge obtainable. It is therefore clear that, as long as the photomasking step of using large grain photomask is necessary, it is not possible to obtain line edge roughness of smaller than 20 nm in a 0.5 μm length.

It is therefore an object of the present invention to provide a CD-SEM calibration standard that does not have the drawbacks or shortcomings of the conventional calibration standard utilizing polysilicon lines formed by a photolithographic method.

It is another object of the present invention to provide a CD-SEM calibration standard that can be fabricated without using a photolithographic method.

It is a further object of the present invention to provide a CD-SEM calibration standard by a focused ion beam deposition technique.

It is another further object of the present invention to provide a CD-SEM calibration standard by a focused ion beam deposition technique utilizing a metal of W, Pt, Au, Ta or Ti.

It is still another object of the present invention to provide a CD-SEM calibration standard by a focused ion beam deposition technique such that line width uniformity is greatly improved over that achievable by a photolithographic method.

It is yet another object of the present invention to provide a CD-SEM calibration standard by a focused ion beam deposition technique such that the line edge roughness of the metal line can be greatly improved.

It is still another further object of the present invention to provide a CD-SEM calibration standard by directly depositing tungsten lines on a semi-conducting substrate by a focused ion beam deposition technique.

It is yet another further object of the present invention to provide a CD-SEM calibration standard by a focused ion beam deposition technique such that tungsten lines having line edge roughness of less than 20 nm in a 0.5 μm length is achieved.

SUMMARY OF THE INVENTION

In accordance with the present invention, a method for forming a critical dimension SEM calibration standard without using a photolithographic technique is provided.

In a preferred embodiment, a method for forming a critical dimension SEM calibration standard is provided which includes the steps of providing a substrate that has a planar top surface, and forming a plurality of metal lines for critical dimension SEM calibration on the planar top surface by a focused ion beam technique.

The method for forming a critical dimension SEM calibration standard may further include the step of forming the plurality of metal lines each having an edge roughness of less than 30 nm in a 0.5 μm length. The method may further include the step of depositing a metal based layer on the planar top surface after the plurality of metal lines are formed. The method may further include the step of providing a semi-conducting substrate that has a planar top surface, or forming the metal lines with a metal selected from the group consisting of W, Au, Pt, Ta and Ti. The method may further include the step of forming the plurality of metal lines on the planar top surface to a thickness between about 0.1 μm and about 2.0 μm. The method may further include the step of forming the plurality of metal lines on the planar top surface to a length of at least 10 μm, or to a width between about 0.1 μm and about 5.0 μm. The method may further include the step of forming the plurality of metal lines on the planar top surface to a thickness of preferably between about 0.2 μm and about 1.0 μm, to a length of preferably larger than 20 μm, and to a width preferably between above 0.2 μm and about 0.5 μm.

The present invention is further directed to a critical dimension SEM calibration standard prepared by a focused ion beam technique which includes a substrate that has a planar top surface, and a plurality of metal lines for critical dimension SEM calibration formed on the planar top surface, wherein the plurality of metal lines each having an edge roughness of less than 30 nm in a 0.5 μm length.

In the critical dimension SEM calibration standard prepared by the focused ion beam technique, the plurality of metal lines each may have an edge roughness of less than 20 nm in a 0.5 μm length, the plurality of metal lines formed on the planar top surface each may have a thickness of about 0.1 μm and about 2.0 μm, a length of larger than 20 μm, and a width between about 0.5 μm and about 5 μm. The plurality of metal lines may be formed by a metal selected from the group consisting of the W, Au, Pt, Ta and Ti. The plurality of metal lines formed on the planar top surface, each may have a line width uniformity of less than 20 nm in a length of 20 μm. The plurality of metal lines on the planar top surface may be formed of tungsten to a thickness between about 0.1 μm and about 2.0 μm, to a length of larger than 20 μm and to a width of between about 0.1 μm and about 5.0 μm.

BRIEF DESCRIPTION OF THE DRAWINGS

These and other objects, features and advantages of the present invention will become apparent from the following detailed description and the appended drawings in which.

DETAILED DESCRIPTION OF THE PREFERRED EMBODIMENTS

Figure 1:
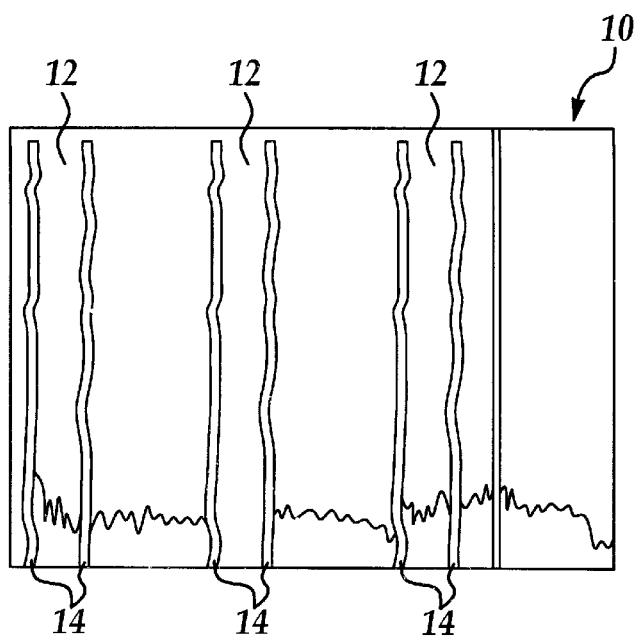
FIG. 1 is a SEM micrograph of a conventional CD-SEM calibration standard formed of polysilicon lines.

The present invention discloses a method for forming a critical dimension SEM calibration standard which can be carried out by first providing a substrate that has a planar top surface and forming a plurality of metal lines for critical dimension CD-SEM calibration on the planar top surface by a focused ion beam technique. The method is capable of producing a plurality of metal lines each having an edge roughness of less than 30 nm in a 0.5 μm length. The plurality of metal lines may be formed of a metal selected from the group consisting of W, Pt, Au, Ta and Ti. The thickness of the plurality of metal lines formed on the planar top surface is between about 0.1 µm and about 2.0 µm, a length of at least 10 µm, and preferably at least 20 µm. The width of the plurality of metal lines is between about 0.2 µm and about o.5 µm.

The present invention further discloses a critical dimension SEM calibration standard that is prepared by a focused ion beam technique that includes a substrate that has a planar top surface, and a plurality of metal lines for critical dimension SEM calibration formed on the planar top surface wherein the plurality of metal lines each has an edge roughness of less than 30 nm in a 0.5 µm length. Preferably, the plurality of metal lines each having an edge roughness of less than 20 nm in a 0.5 µm length. The critical dimension SEM calibration standard prepared by the present invention novel method has a line width uniformity of less than 5 nm in a length of 20 µm. The plurality of metal lines may be formed of a metal of W, Pt, Au, Ta or Ti.

The present invention focused ion beam method provides a significantly improved line quality than that previously achieved with polysilicon lines formed by a photolithographic method. The present invention method produces a straight, narrow line with minimized line edge roughness, i.e. a roughness of less than 20 nm in a 0.5 µm length. The present invention novel method further produces profile uniformity and achieves improved line width. As a result, the CD-SEM calibration standard manufacturing cost is significantly reduced.

In the present invention novel method, a tungsten deposition process is illustrated in the preferred embodiment. However, the present invention novel method is not limited to the deposition of tungsten only, but also applicable to deposition of other similar metals such as Pt, Au, Ta and Ti. The deposition of a tungsten metal line is achieved by directing a focused beam of gallium ions to the region where a line is to be formed in an environment of hexacarbonyl tungsten. In a typical tungsten deposition process, the gallium ions cause the deposition of hexacarbonyl tungsten so that tungsten metal deposits locally at the desired location. The beam of gallium ions can be focused down to a submicron diameter.

In the present invention method, it is also possible to deposit metals such as Pt, Au, Ta and Ti in the focused ion beam apparatus under an ion beam of gallium ions. The method can be carried out with sub-micron resolution to provide straight, narrow lines with minimal line edge roughness and significantly improved line width uniformity.

In the present invention novel method for depositing a metal line, selected gasses for the specific metals to be deposited are first delivered to the point of focus through a small nozzle positioned near the sample surface. It is proposed that molecules of the gas are adsorbed on the surface and decomposed by collisions with the gallium ions at the point of impact. Metal lines of a desirable width and thickness can thus be formed by moving the ion beam in a pre-determined pattern and speed.

Figure 2:
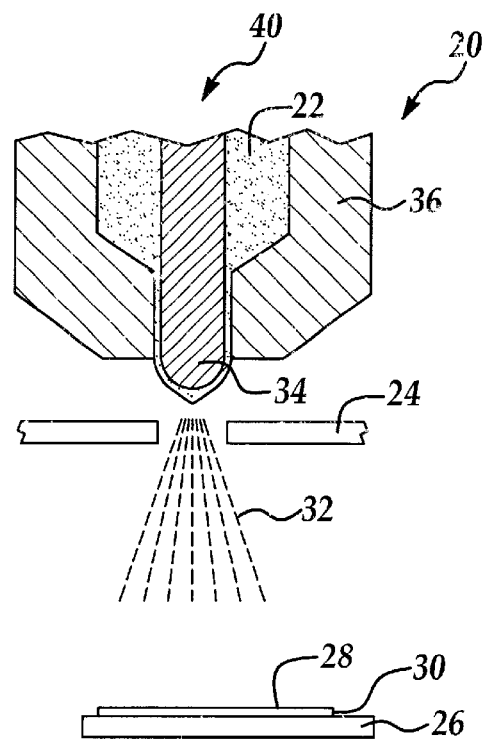
FIG. 2 is a simplified cross-sectional view of a focused ion beam apparatus for depositing the present invention metal lines.

Referring now to FIG. 2, wherein a present invention focused ion beam apparatus 20 is shown. The FIB apparatus 20 consists of an ion source 22, i.e. a liquid metal, and ion optical column 24, i.e. an extractor or electrode, and the sample stage 26. Metal lines (not shown) are formed on a top surface 28 of a sample substrate 30. The FIB apparatus 20 functions similarly to an e-beam exposure system with ions replacing electrons. The FIB apparatus delivers a desired dosage with 0.1 µm accuracy and superior alignment capability. Ions 32 of gallium are used in depositing a narrow line of tungsten on the top surface 28. Also shown in FIG. 2, are a heated needle 34 for injecting the metal ions 32 and a capillary 36 surrounding the ion gun 40.

Figure 3:
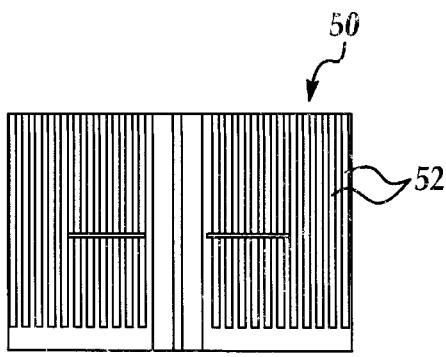
FIG. 3 is an enlarged, plane view of a present invention CD-SEM calibration standard formed by the focused ion beam technique.
Figure 4:
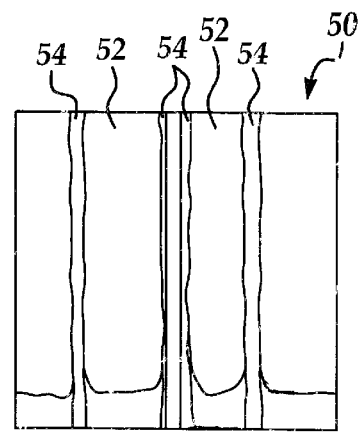
FIG. 4 is an enlarged, plane view of the present invention CD-SEM calibration standard illustrating two tungsten lines.

FIG. 3 shows an enlarged, plane view of a CD-SEM calibration standard 50 fabricated by the present invention novel method. A plurality of metal line 52, as shown by the dark lines are formed of tungsten metal by the focused ion beam technique. The straightness of the lines 52 and the small line edge roughness are shown in a further enlarged view of FIG. 4. Each of the straight lines 52 is bordered with an edge area 54 (shown in white lines) indicative of a tapered edge for the tungsten lines 52. When compared to the polysilicon lines 12 shown in FIG. 1, the tungsten lines 52 are provided with a much smoother edge 54 when compared to the edge portions 14 of FIG. 1. The tungsten lines 52 shown in FIG. 4 were deposited at 4 different thickness of 0.2 µm, 0.5 µm, 0.7 µm and 1.0 µm. In a typical CD-SEM calibration standard, a line thickness of 0.5 µm is normally the target, while in reality a thickness of about 0.3 µm is frequently achieved. On a typical calibration sample, the plurality of lines 52 each has a length of about 20 µm, or a minimal length of 10 µm. The width of the plurality of tungsten lines 52 is about 0.3 µm, or within a range of between about 0.1 µm and about 5.0 µm. The word "about" is to mean a range of value of ±10% from the average value given. A total thickness range may be between about 0.1 µm and about 2 µm, while a preferred range is between about 0.2 µm and about 1.0 µm. While tungsten metal is illustrated in the preferred embodiment of the present invention for forming the narrow straight lines 52, other suitable metals such as Pt, Au, Ta and Ti may also be used as long as a suitable gas can be provided in forming the lines under ion bombardment.

Figure 5:
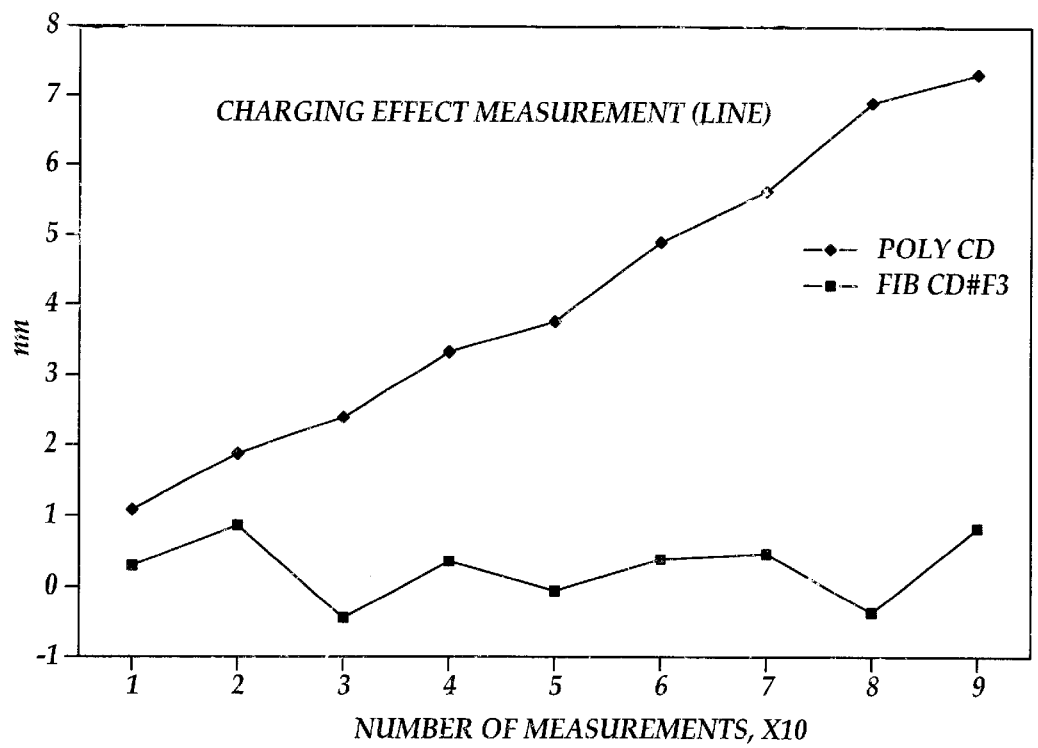
FIG. 5 is a graph illustrating the charging effect on the present invention CD-SEM calibration standard formed of tungsten lines when compared to the charging effect on a conventional calibration standard formed of polysilicon lines.

The desirable properties of the tungsten metal lines when compared to the conventional polysilicon lines is shown in FIG. 5. For instance, the charging effect, i.e. the effect shown after the calibration line is bombarded by gallium ions repeatedly, is shown in FIG. 5. It is seen that charging effect is non-existent, i.e. near 0 for the tungsten lines formed by the present invention novel method of focused ion beam technique. To the contrary, the polysilicon lines formed by the conventional deposition/photolithographic technique shows a significant charging effect after the calibration standard has been used for only 20 times. The charging effect becomes unacceptable, i.e. at a value of about 4 nm after the standard has been used for 50 calibrations.

The present invention novel method and apparatus for forming a critical dimension SEM calibration standard have therefore been amply described in the above description and in the appended drawings of FIGS. 2~5.

While the present invention has been described in an illustrative manner, it should be understood that the terminology used is intended to be in a nature of words of description rather than of limitation.

Furthermore, while the present invention has been described in terms of a preferred and alternate embodiment, it is to be appreciated that those skilled in the art will readily apply these teachings to other possible variations of the inventions.

The embodiment of the invention in which an exclusive property or privilege is claimed are defined as follows.

What is claimed is:

1. A method for forming a critical dimension SEM calibration standard comprising the steps of:
providing a substrate having a planar top surface; and
forming a plurality of metal lines each having a line width uniformity of less than 20 nm in a length of 20 µm for critical dimension SEM calibration on said planar top surface by a focused ion beam technique.

2. A method for forming a critical dimension SEM calibration standard according to claim 1 further comprising the step of forming said plurality of metal lines each having an edge roughness of less than 30 nm in a 0.5 μm length.

3. A method for forming a critical dimension SEM calibration standard according to claim 1 further comprising the step of depositing a metal base layer on said planar top surface after said plurality of metal lines are formed.

4. A method for forming a critical dimension SEM calibration standard according to claim 1 further comprising the step of providing a semiconductor substrate having a planar top surface.

5. A method for forming a critical dimension SEM calibration standard according to claim 1, wherein said plurality of metal lines is formed of a metal selected from the group consisting of W, Pt, Au, Ta and Ti.

6. A method for forming a critical dimension SEM calibration standard according to claim 1 further comprising the step of forming said plurality of metal lines on said planar top surface to a thickness between about 0.1 μm and about 2.0 μm.

7. A method for forming a critical dimension SEM calibration standard according to claim 1 further comprising the step of forming said plurality of metal lines on said planar top surface to a length of at least 10 μm.

8. A method for forming a critical dimension SEM calibration standard according to claim 1 further comprising the step of forming said plurality of metal lines on said planar top surface to a width between about 0.1 μm and about 5.0 μm.

9. A method for forming a critical dimension SEM calibration standard according to claim 1 further comprising the step of forming said plurality of metal lines on said planar top surface to a thickness preferably between about 0.2 μm and about 1.0 μm.

10. A method for forming a critical dimension SEM calibration standard according to claim 1 further comprising the step of forming said plurality of metal lines on said planar top surface to a length preferably larger than 20 μm.

11. A method for forming a critical dimension SEM calibration standard according to claim 1 further comprising the step of forming said plurality of metal lines on said planar top surface to a width preferably between about 0.2 μm and about 0.5 μm.

12. A method for forming a critical dimension SEM calibration standard according to claim 1 further comprising the step of forming said plurality of metal lines on said planar top surface to a thickness between about 0.2 μm and about 1.0 μm, to a length larger than 20 μm and to a width between about 0.2 μm and about 0.5 μm.

13. A critical dimension SEM calibration standard prepared by a focused ion beam technique comprising:
    a substrate that has a planar top surface; and
    a plurality of metal lines for critical dimension SEM calibration formed on said planar top surface, said plurality of metal lines each having an edge roughness of less than 30 nm in a 0.5 μm length.

14. A critical dimension SEM calibration standard prepared by a focused ion beam technique according to claim 13, wherein said plurality of metal lines each having an edge roughness of less than 20 μnm in a 0.5 μm length.

15. A critical dimension SEM calibration standard prepared by a focused ion beam technique according to claim 13, wherein said plurality of metal lines formed on said planar top surface each having a thickness between about 0.1 μm and about 2.0 μm.

16. A critical dimension SEM calibration standard prepared by a focused ion beam technique according to claim 13, wherein said plurality of metal lines formed on said planar top surface each having a length of larger than 20 μm.

17. A critical dimension SEM calibration standard prepared by a focused ion beam technique according to claim 13, wherein said plurality of metal lines formed on said planar top surface each having a width between about 0.5 μm and about 5 μm.

18. A critical dimension SEM calibration standard prepared by a focused ion beam technique according to claim 13, wherein said plurality of metal lines is formed by a metal selected from the group consisting of W, Pt, Au, Ta and Ti.

19. A critical dimension SEM calibration standard prepared by a focused ion beam technique according to claim 13, wherein said plurality of metal lines formed on said planar top surface each having a line width uniformity of less than 20 nm in a length of 20 μm.

20. A critical dimension SEM calibration standard prepared by a focused ion beam technique according to claim 13, wherein said plurality of metal lines on said planar top surface is formed of tungsten to a thickness between about 0.1 μm and about 2.0 μm, to a length larger than 20 μm and to a width between about 0.1 μm and about 5.0 μm.

* * * * *